United States Patent [19]

Borsanyi et al.

[11] Patent Number: 4,811,733
[45] Date of Patent: Mar. 14, 1989

[54] ELECTROSURGICAL DEVICE

[75] Inventors: Alexander S. Borsanyi, Newport Beach; Colette R. D. Cozean, Diamond Bar, both of Calif.

[73] Assignee: Baxter Travenol Laboratories, Inc., Deerfield, Ill.

[21] Appl. No.: 946,800

[22] Filed: Dec. 29, 1986

Related U.S. Application Data

[63] Continuation-in-part of Ser. No. 712,371, Mar. 14, 1985, abandoned.

[51] Int. Cl.$^4$ .............................................. A61B 17/36
[52] U.S. Cl. ............................ 128/303.14; 128/303.17
[58] Field of Search ............ 128/303.1, 303.13–303.17, 128/783, 784

[56] References Cited

U.S. PATENT DOCUMENTS

| | | | |
|---|---|---|---|
| 1,971,024 | 8/1934 | Wappler | 174/89 |
| 2,004,559 | 6/1935 | Wappler et al. | 174/89 |
| 2,029,487 | 2/1936 | Kleine | 240/2 |
| 3,532,095 | 6/1968 | Miller et al. | 128/303.13 |
| 3,674,016 | 6/1970 | Leucci | 128/4 |
| 3,982,542 | 9/1976 | Ford et al. | 128/303.14 |
| 4,181,131 | 1/1980 | Ogiu | 128/303.15 |
| 4,301,802 | 11/1981 | Poler | 128/303.14 |
| 4,325,374 | 4/1982 | Kemiya | 128/303.15 |
| 4,347,842 | 9/1982 | Beale | 128/276 |
| 4,362,160 | 12/1982 | Hiltebrandt et al. | 128/303.15 |
| 4,485,812 | 12/1984 | Harada et al. | 128/303.15 |
| 4,503,855 | 3/1985 | Maslanka | 128/303.15 |
| 4,711,238 | 12/1987 | Cunningham | 128/303.14 |

FOREIGN PATENT DOCUMENTS

| | | | |
|---|---|---|---|
| 2657256 | 6/1978 | Fed. Rep. of Germany | 128/303.14 |
| 3220940 | 12/1983 | Fed. Rep. of Germany | 128/303.14 |
| 2235669 | 1/1975 | France | 128/303.17 |

Primary Examiner—Max Hindenburg
Attorney, Agent, or Firm—Loyal M. Hanson; Gordon L. Peterson

[57] ABSTRACT

A device for electrosurgery includes a curved-tip probe adapted for insertion into an incision, and a resiliently deformable electrode movable longitudinally within the probe so that the distal end can be projected in an offset direction out of the tip of the probe between a closed position wherein the terminal end of the electrode is closely adjacent the tip to an extended position wherein the terminal end is a greater distance from the tip. A shielding member of flexible and resilient composition extends alongside the probe for shielding the terminal end of the electrode from tissue during surgery. The shielding member may be spring biased toward the closed position and include various electrode engaging arrangements that inhibit lateral movement of the electrode relative to the probe. One embodiment includes a slidable shielding member that enables the device to be used for lateral release or meniscal surgery.

22 Claims, 2 Drawing Sheets

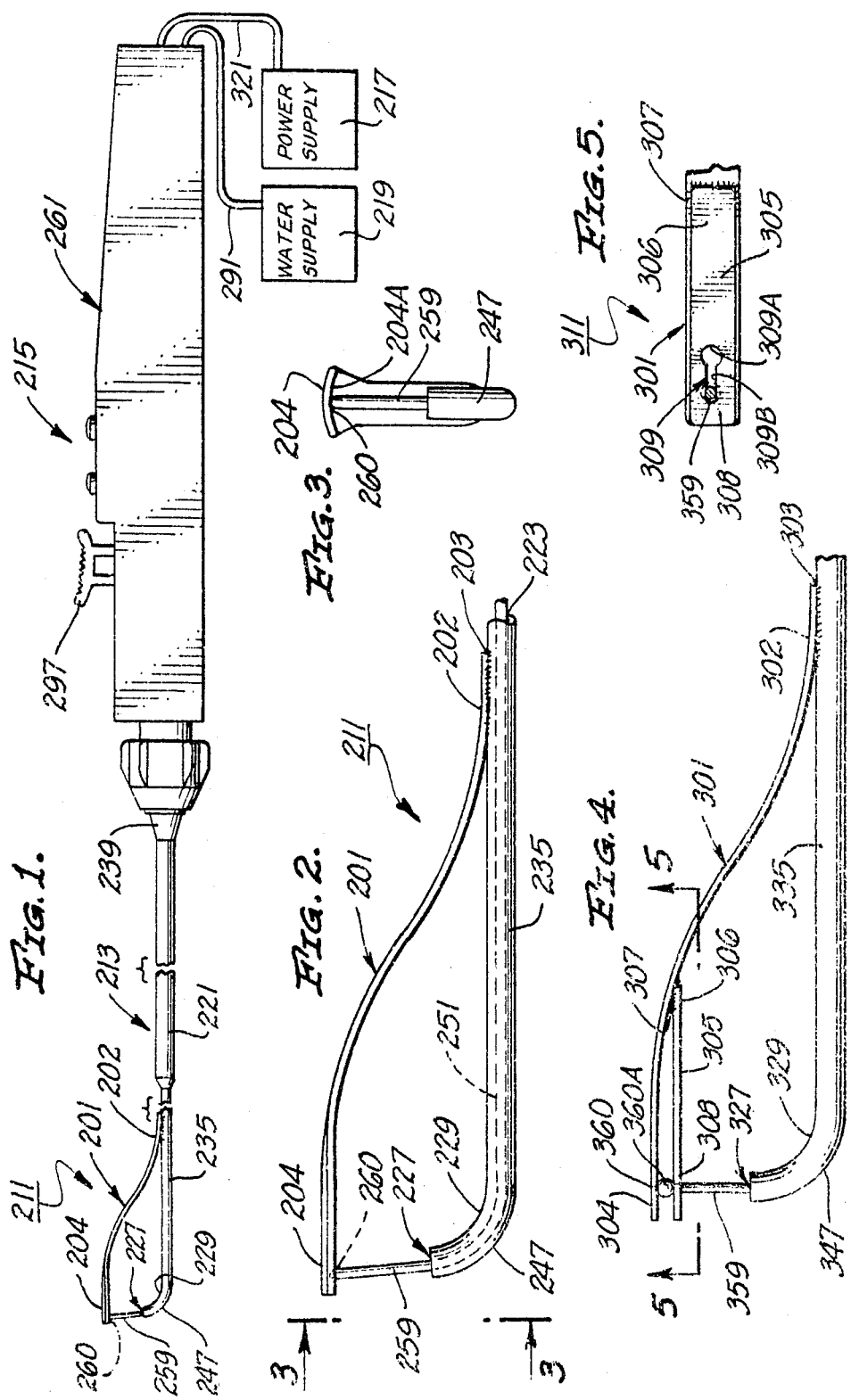

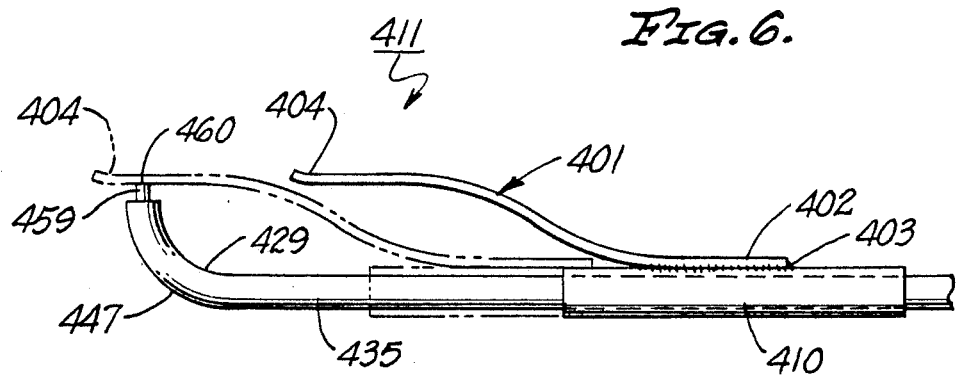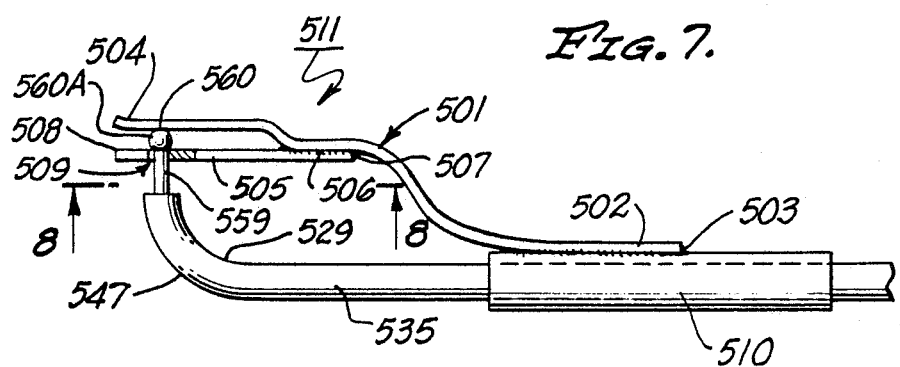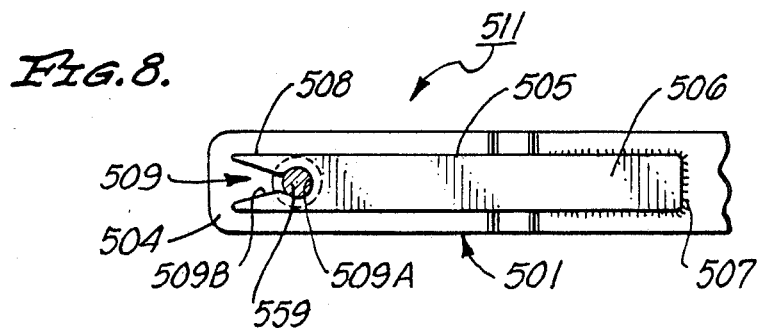

4,811,733

ELECTROSURGICAL DEVICE

CROSS-REFERENCES TO RELATED APPLICATIONS

This is a continuation-in-part of copending application Ser. No. 712,371, filed Mar. 14, 1985, now abandoned.

BACKGROUND OF THE INVENTION

1. Technical Field

The invention relates generally to surgical equipment, and more particularly to a new and improved device suitable for electrosurgical removal of torn knee cartilage.

2. Background Information

Torn knee cartilage, or meniscus, is often removed in treating various knee joint injuries. One technique of accomplishing this utilizes a probe supported electrode placed against the tissue to be cut. Greater precision often results, with less trauma to surrounding structures compared to many other techniques.

The electrode in one existing device employs a thin, element that is not self supporting. The electrode is attached to a leaf spring mounted on the exterior of the probe, the leaf spring being spring biased outwardly away from the probe to keep the electrode taut for cutting purposes. However, if the electrode breaks or becomes detached from the leaf spring, there is nothing to resist the leaf spring and it springs outwardly from the probe to a position where it can damage tissue.

A novel electrosurgical device that overcomes this problem is disclosed in the parent application identified above. It employs a stiffer electrode that is less prone to break and does not require the leaf spring support. Although effective in many respects, the device is particularly useful for lateral release surgery, flexibility of the unsupported electrode limiting usefulness for meniscus cutting purposes. In addition, the exposed end of the electrode can damage sensitive tissue.

Consequently, it is desirable to have a new and improved device that overcomes these concerns—one overcoming the broken electrode problem that can be used for both lateral release surgery and meniscus cutting purposes. In addition, it is desirable that the device include features protecting sensitive tissue from the electrode end.

SUMMARY OF THE INVENTION

This invention recognizes the problems associated with the prior art and provides a new and improved electrosurgical device with the desired attributes. It converts the device described in the parent application to one suitable for cutting menisus.

Briefly, a device constructed according to the invention includes an elongated probe having a curved distal end portion adapted to be inserted into an incision. The probe defines an elongated passage extending longitudinally to a port in the distal end.

An electrode disposed coaxially within the passage has a resiliently deformable distal end portion adapted to be extended out of the port in a direction offset angularly from the direction of probe elongation. The electrode is movable within the passage so that the distal end portion of the electrode can be projected out of the port a variable distance in the offset direction.

This enables positioning of the distal end of the electrode selectively for electrosurgery purposes. It can be moved between a closed position wherein the distal end is closely adjacent the probe tip to an extended position wherein it is a greater distance from the tip.

A shielding member of flexible and resilient composition is included alongside the probe. One end is mounted on the probe and the other end shields the terminal end of the electrode. This inhibits tissue damage during surgery.

In one form of the invention, shielding is accomplished with a leaf spring arrangement. The leaf spring is spring biased toward the port in the distal end of the probe to maintain it against the terminal end of the electrode when the electrode is moved between the open and closed positions.

Various electrode engaging arrangements may be included. These employ a portion of the shielding member for engaging the electrode to inhibit lateral movement of the electrode relative to the probe when the electrode is in the extended position. This adapts the device for menicus cutting purposes.

One embodiment includes a sleeve mounted slidably on the probe, the shielding member being attached to the sleeve. Mounted in this fashion, the shielding member can be moved alongside the probe between a forward position where it engages the electrode, and a rearward position wherein the terminal end of the electrode is exposed. This enables use for both lateral release surgery and menicus cutting.

Thus, the invention provides a new and improved device for electrosurgery with the desired attributes. The tip of the electrode is shielded so that tissue damage is less likely. In addition, the electrode is supported to inhibit lateral movement. Furthermore, normally closed embodiments overcome the problem of a detached electrode with less complicated structure, and a slidable shield arrangement permits conversion for lateral release or meniscal surgery.

The above mentioned and other objects and features of this invention and the manner of attaining them will become apparent, and the invention itself will be best understood, by reference to the following description taken in conjunction with the accompanying illustrative drawings.

BRIEF DESCRIPTION OF THE DRAWINGS

FIG. 1 of the drawings is an elevation view of an electrosurgical device constructed according to the invention;

FIG. 2 is an enlarged fragmentary view of the distal end portion of the device;

FIG. 3 is a further enlarged fragmentary view of the distal end portion taken on line 3—3 of FIG. 2;

FIG. 4 is an enlarged fragmentary view, showing a different electrode engaging arrangement;

FIG. 5 is an enlarged detail view taken on line 5—5 of FIG. 4

FIG. 6 is an enlarged fragmentary view of the distal end portion of another embodiment employing a slidable leaf spring;

FIG. 7 is an enlarged fragmentary view showing a slidable leaf spring utilizing another electrode engaging arrangement; and FIG. 8 is an enlarged detail view taken on line 8—8 of FIG. 7.

DESCRIPTION OF THE PREFERRED EMBODIMENTS

Referring now to the drawings, and particularly to FIGS. 1-3, there is shown a device 211 constructed according to the invention. Apart from the shielding aspect and related structural variations, the device 211 is identical to the electrosurgical cutting and coagulating device 11 described in the parent application. Therefore, the identical features are not further illustrated or described. The parent application is hereby incorporated by reference for the details of construction it illustrates and describes, and for convenience, reference numerals in FIGS. 1-3 are increased by 200 over those designating similar features in the parent application.

Generally, the device 211 includes a probe assembly 213 attached to a handpiece 215 that is coupled by line 321 to an electrical power supply 217 and by line 291 to a water supply 219. A distal segment of the probe assembly 213 is insertable through an incision to perform electrosurgery, and the handpiece 215 includes the components necessary to provide control of the surgery, all as more specifically described in the parent application.

The probe assembly 213 includes an elongated probe 221 which has an elongated, axial passageway 223 (FIG. 2) extending longitudinally through the probe 221 to a port 227 at distal end portion 229. Although the probe 221 can be of various different constructions, in the embodiment illustrated it comprises a main tube 231, a distal tube 235, and a bushing 239 retained on housing 261.

Upstanding button 297 projecting out of the housing 261 is coupled to suitable components that serve as adjustable electrode means. They enable manual movement of an electrically conductive member or electrode 251 (FIG. 2) within the passage 223, the electrode 251 corresponding to the elongated member 51 in the parent application. Pushing inwardly on the button 297 unlocks the mechanism to enable manual movement of the electrode 251, and releasing the button locks the mechanism to retain the electrode in a selected position.

Distal end portion 229 of the probe includes a curved region 247 that directs the electrode 235 in a direction offset angularly from the direction of elongation of the probe 213, i.e., a direction different from the direction of probe elongation. In the illustrated embodiment, the offset direction is generally perpendiculary to the direction of probe elongation.

By operating the push button 297, the length of a distal end portion or exposed portion 259 of the electrode can be varied, the exposed portion 259 corresponding to the electrode 62 in the parent application. Thus, the exposed portion of the electrode can be moved in the offset direction between the extended position illustrated in FIGS. 1-3 and a closed position wherein the terminal end 260 of the electrode is closely adjacent the port 227 (not shown).

The invention includes shielding means for shielding a region of the electrode, preferably the terminal end 260 of the electrode 251, from tissue during surgery. This is accomplished in the illustrated embodiment by a shield or shielding member which preferably includes a leaf spring 201. The leaf spring may be composed of an electrically conductive material over which a suitable insulating material is disposed, or it may be composed of a nonconductive material. Alternatively, a nonconductive member (not shown) can be placed between the leaf spring and the portion of the conductor it contacts.

The leaf spring extends alongside the probe 213 from a first end 202 of the leaf spring that is attached to the probe by suitable means such as solder 203, to a second end 204 that is disposed in a position to shield the terminal end 260. It is composed of a flexible, resilient material formed so that it is spring biased toward distal portion 229 of the probe. This causes the leaf spring to follow the terminal end 260 of the electrode 251 when the electrode is moved between the extended and closed positions.

Thus, the electrode can be retained in a closed position during insertion into an incision, moved to an extended position as illustrated in FIG. 1 for cutting purposes, and then again be returned to the closed position for withdrawal from the incision. As this is done, the second end 204 of the leaf spring 201 follows the terminal end 260 of the electrode to shield it electrically and mechanically from tissue.

The second end 204 of the leaf spring 201 includes a curved portion 204A (FIG. 3) for engaging the electrode to inhibit lateral movement of the electrode relative to the probe 213, i.e., movement perpendiculary to a plane common to the offset direction and the direction of probe elongation. This portion curves concavely toward the distal end portion 229 of the probe, so that the curved portion 204A abuts and engages the terminal end 260 of the electrode under pressure of the spring biased leaf spring.

Referring now to FIGS. 4 and 5, there is shown a device 311 which employs a slightly different terminal end engaging arrangement. Apart from this aspect, the device 311 is identical to the device 211, and identical features are not illustrated in detail. Reference numerals in FIGS. 4 and 5 are increased by 100 over those designating similar features of device 211 in FIGS. 1-3.

The exposed portion 359 of the electrode in the device 311 includes an enlarged end portion 360A disposed proximate the terminal end 360. A lower leaf 305 disposed between the leaf spring 301 and the distal end portion 329 of the probe engages the enlarged end portion 360A, and this further inhibits lateral movement. In addition, it inhibits movement parallel to the direction of probe elongation and retains the shielding member securely against the terminal end 360 of the electrode so that it follows the terminal end as the electrode is moved between the extended and closed positions.

The lower leaf 305 has a proximal end 306 attached to the leaf spring 301 by suitable means such as solder 307, and an apertured portion 308 that extends generally parallel to and spaced slightly apart from the second end portion 304 of the leaf spring 301. It may be composed of the same material as the leaf spring.

The apertured portion 308 defines a keyhole-like aperture having a large portion 309A and a smaller portion 309B. The enlarged end portion 360A of the electrode is placed through the large portion 309A and then the electrode is seated within the smaller portion 309B. This engages the enlarged end portion 360A between the second end portion 304 of the leaf spring and the apertured portion 308 of the lower leaf, with the electrode better secured.

Considering now FIG. 6, there is shown a device 411 that employs a slidable sleeve arrangement for adjusting the position of the leaf spring between the rearward position shown in solid lines and the forward position shown in phantom lines. Apart from this aspect, the device 411 is identical to the device 211, and the identical features are not illustrated in detail. Reference numerals in FIG. 6 are increased by 200 over those designating identical similar features of the device 211 in FIGS. 1-3.

Sleeve 410 is a hollow cylindrical member having a size and shape adapted to fit over the probe and be slid between the forward and rearward positions. Other structures providing a moveable carriage can be employed. The first end 402 of the leaf spring 401 is attached to the sleeve 410 by suitable means such as solder 403, and the second end portion 404 includes a curved surface (not visible) similar to the curve surface 204A in the device 211.

With this sliding sleeve arrangment, the second end portion 404 of the leaf spring can be withdrawn from the terminal end 460 of the electrode to convert the device for various electrosurgical applications.

The device 511 in FIGS. 7 and 8 employs a combination of a slidable sleeve similar to the sleeve of the device 411 in FIG. 6, and a lower leaf similar to the lower leaf of the device 311 in FIGS. 4 and 5. The device 311 is otherwise identical to the device 211, and the identical features are not illustrated in detail. Reference numerals in FIGS. 7 and 8 are increased by 300 over those designating similar features of the device 211 in FIGS. 1-3.

Thus, a lower leaf 505 having a proximal end 506 attached by suitable means to the leaf spring 501 such as solder 507, includes a forked portion 508 which extends between the second end portion 504 of the leaf spring and the distal end portion 529 of the probe. The forked portion 508 defines an open end channel 509 for receiving the enlarged end portion 560A of the electrode.

The channel 509 has an inner channel portion 509A slightly smaller than the enlarged end portion 560A in which to seat the electrode. This is done by inserting the electrode through the outer channel portion 509B into the inner channel portion 509A, with the enlarged end portion 560A disposed between the leaf spring and the lower leaf. The channel 509 may be slightly smaller than the diameter of the electrode where the inner channel portion 509A and the outer portion 509B join, so that the electrode snaps into place.

If it is desired to use the device 511 with an exposed terminal end 560, the slidable sleeve 510 is moved to the rearward position with the electrode disengaging from the open end channel 509.

Thus the clever shielding arrangement of this invention shields of the electrode, inhibits lateral movement of the electrode, and in various forms engages the terminal end positively to retain the shielding member over the terminal end. In addition, the terminal end can be exposed in one embodiment by simply withdrawing the slidable sleeve to a rearward position.

Although an exemplary embodiment of the invention has been shown and described, many changes, modifications, and substitutions may be made by one having ordinary skill in the art without necessarily departing from the spirit and scope of this invention.

What is claimed is:

1. A device for electrosurgery, comprising:
   an elongated probe having a curved distal end portion insertable into an incision, the probe defining an elongated passage extending longitudinally within the probe to a port in the distal end portion;
   adjustable electrode means, including an electrode defined by an electrically conductive member disposed coaxially within the passage having a resiliently deformable distal end portion extendible out of the port in a first direction offset angularly from the direction of elongation of the probe, for enabling manual movement of the electrode within the passage so that the distal end portion of the electrode can be projected out of the port a variable distance in the first direction to position the distal end portion of the electrode selectively for electrosurgery purposes between a closed position wherein a terminal end of the electrode is closely adjacent the distal end portion of the probe to an extended position wherein the terminal end is a greater distance from the port; and
   shielding means, including a shielding member defined by a resilient, elongated member extending alongside the probe, the shielding member having a first end portion mounted on the probe and a second end portion for shielding the terminal end of the electrode from tissue during surgery.

2. A device as recited in claim 1, wherein:
   the shielding member is spring biased toward the port in the distal end portion of the probe to maintain the second end portion against the terminal end of the electrode.

3. A device as recited in claim 1, wherein the shielding means includes:
   electrode engaging means, including a portion of the second end portion of the shielding member adapted to engage the distal end portion of the electrode, for inhibiting lateral movement of the electrode relative to the probe.

4. A device as recited in claim 3, wherein the electrode engaging means comprises:
   a curved portion of the second end portion of the shielding member with which to engage the distal end portion of the electrode.

5. A device as recited in claim 3, wherein the electrode engaging means comprises:
   an enlarged end portion of the electrode at the terminal end of the electrode;
   an apertured portion of the shielding member defining a keyhole-shaped aperture having a large portion through which to place the enlarged end portion of the electrode and a smaller portion in which to seat the electrode with the enlarged end portion thereby engaged.

6. A device as recited in claim 5, wherein:
   the apertured portion of the shielding member extends generally parallel to and spaced slightly apart from the second end portion, between the second end portion and the port in the distal end portion of the probe.

7. A device as recited in claim 1, further comprising:
   shielding member adjustment means, including means for mounting the first end portion of the shielding member on the probe movably, for enabling the shielding member to be moved alongside the probe between a forward position wherein the second end portion of the shielding member is disposed in a position to shield the terminal end of the electrode and a rearward position wherein the second end portion is withdrawn from the terminal end.

8. A device as recited in claim 7, wherein the means for mounting the first end portion comprises:
   a sleeve member mounted slidably on the probe; and
   means for attaching the second end of the shielding member to the sleeve member.

9. A device as recited in claim 7, further comprising:
electrode engaging means, including a portion of the second end portion of the shielding member adapted to engage the distal end portion of the electrode, for inhibiting lateral movement of the electrode relative to the probe.

10. A device as recited in claim 9, wherein the electrode engaging means comprises:
a curved portion of the second end portion of the shielding member with which to engage the distal end portion of the electrode.

11. A device as recited in claim 9, wherein the electrode engaging means comprises:
an enlarged end portion of the electrode at the terminal end of the electrode;
a forked portion of the shielding member defining an open end channel for receiving the distal end portion of the electrode, the channel having an inner portion slightly smaller than the enlarged end portion of the electrode in which to seat the electrode with the distal end portion of the electrode thereby engaged.

12. A device as recited in claim 11, wherein:
the forked portion of the shielding member extends generally parallel to and spaced slightly apart from the second end portion, between the second end portion and the port in the distal end portion of the probe.

13. An electrosurgical device comprising:
an elongated probe having a distal end portion and a generally longitudinally extending passage opening at a port at the distal end portion of the probe, said probe being insertable into an incision;
at least a region of the distal end portion of said probe being curved;
an elongated member defining an electrode having proximal and distal end portions, at least the distal end portion of the electrode being resiliently deformable, said electrode extending within said passage and said distal end portion of the electrode being extendible out said port in a first direction which is different from the direction of elongation of the probe to form an exposed portion of the electrode for electrosurgery with said curved region of the distal end portion of the probe at least assisting in directing the exposed portion generally in said first direction;
said elongated member and said probe being relatively movable to move the electrode longitudinally in the passage whereby said exposed portion can project out of said port for a variable distance in said first direction to enable varying the length of the exposed portion, said proximal end portion of said electrode being releasably fixable against movement in said passage whereby the length of the exposed portion can be releasably fixed;
means for coupling the electrode to a source of electrical energy; and
shielding means, including a shielding member defined by a resilient elongated member extending alongside the probe, the shielding member having a first end portion mounted on the probe and a second end portion for shielding a terminal end of the electrode from tissue during surgery.

14. A device as recited in claim 13, wherein:
the shielding member is spring biased toward the port in the distal end portion of the probe to maintain the second end portion against the terminal end of the electrode.

15. A device as recited in claim 13, wherein the shielding means includes:
electrode engaging means, including a portion of the second end portion of the shielding member adapted to engage the distal end portion of the electrode, for inhibiting lateral movement of the electrode relative to the probe.

16. A device as recited in claim 15, wherein the electrode engaging means comprises:
a curved portion of the second end portion of the shielding member with which to engage the distal end portion of the electrode.

17. A device as recited in claim 15, wherein the electrode engaging means comprises:
an enlarged end portion of the electrode at the terminal end of the electrode;
an apertured portion of the shielding member defining a keyhole-shaped aperture having a large portion through which to place the enlarged end portion of the electrode and a smaller portion in which to seat the electrode with the enlarged end portion thereby engaged.

18. A device as recited in claim 13, further comprising:
shielding member adjustment means, including means for mounting the first end portion of the shielding member on the probe movably, for enabling the shielding member to be moved alongside the probe between a forward position wherein the second end portion of the shielding member is disposed in a position to shield the terminal end of the electrode and a rearward position wherein the second end portion is withdrawn from the terminal end.

19. A device as recited in claim 18, wherein the means for mounting the first end portion comprises:
a sleeve member mounted slidably on the probe; and
means for attaching the second end of the shielding member to the sleeve member.

20. A device as recited in claim 18, further comprising:
electrode engaging means, including a portion of the second end portion of the shielding member adapted to engage the distal end portion of the electrode, for inhibiting lateral movement of the electrode relative to the probe.

21. A device as recited in claim 20, wherein the electrode engaging means comprises:
a curved portion of the second end portion of the shielding member with which to engage the distal end portion of the electrode.

22. A device as recited in claim 20, wherein the electrode engaging means comprises:
an enlarged end portion of the electrode at the terminal end of the electrode;
a forked portion of the shielding member defining an open end channel for receiving the distal end portion of the electrode, the channel having an inner portion slightly smaller than the enlarged end portion of the electrode in which to seat the electrode with the distal end portion of the electrode thereby engaged.

* * * * *